United States Patent
Ohkubo et al.

(10) Patent No.: US 8,680,355 B2
(45) Date of Patent: Mar. 25, 2014

(54) OLEFIN PRODUCTION PROCESS

(75) Inventors: Tsuneyuki Ohkubo, Ichihara (JP);
Kenji Fujiwara, Kamakura (JP);
Terunori Fujita, Yokohama (JP)

(73) Assignee: Mitsui Chemcials, Inc., Tokyo (JP)

( * ) Notice: Subject to any disclaimer, the term of this patent is extended or adjusted under 35 U.S.C. 154(b) by 102 days.

(21) Appl. No.: 13/131,905

(22) PCT Filed: Oct. 22, 2009

(86) PCT No.: PCT/JP2009/068173
§ 371 (c)(1),
(2), (4) Date: May 31, 2011

(87) PCT Pub. No.: WO2010/064500
PCT Pub. Date: Jun. 10, 2010

(65) Prior Publication Data
US 2011/0230696 A1   Sep. 22, 2011

(30) Foreign Application Priority Data

Dec. 1, 2008 (JP) .................................. 2008-306735
Sep. 4, 2009 (JP) .................................. 2009-204474

(51) Int. Cl.
*C07C 1/20* (2006.01)

(52) U.S. Cl.
USPC ............... 585/638; 585/639; 502/60; 502/61; 502/62; 502/63; 502/64; 568/798; 568/799; 568/768

(58) Field of Classification Search
USPC ......... 585/638, 639, 640, 641, 642, 422, 446; 568/798, 799, 768, 385, 565, 569, 577, 568/741; 502/60–71
See application file for complete search history.

(56) References Cited

U.S. PATENT DOCUMENTS

| | | | |
|---|---|---|---|
| 4,554,260 A * | 11/1985 | Pieters et al. | 502/61 |
| 5,017,729 A * | 5/1991 | Fukuhara et al. | 585/422 |
| 6,518,475 B2 | 2/2003 | Fung et al. | |
| 6,888,035 B2 * | 5/2005 | Fallon et al. | 568/798 |
| 7,405,337 B2 | 7/2008 | Kalnes et al. | |
| 2004/0116749 A1 | 6/2004 | Levin et al. | |
| 2010/0168491 A1 | 7/2010 | Iwamoto et al. | |

FOREIGN PATENT DOCUMENTS

| | | |
|---|---|---|
| CN | 1043956 | 7/1990 |
| DE | 84378 | 9/1971 |
| EP | 1974812 A1 | 10/2008 |
| JP | 61-33235 | 2/1986 |
| JP | 61-67493 | 4/1986 |
| JP | 2-174737 | 7/1990 |
| JP | 3-41035 | 2/1991 |
| JP | 3-41038 | 2/1991 |
| JP | 6-091171 A | 4/1994 |
| JP | 2008-513449 A | 5/2008 |
| WO | 02/066407 A1 | 8/2002 |
| WO | 2009/008377 | 11/2009 |

OTHER PUBLICATIONS

Search Report and Written Opinion prepared by the Austrian Patent Office issued in connection with the corresponding Singapore application (201103938-5) dated Jul. 12, 2012.
International Search Report dated Feb. 2, 2010.
Applied and Environmental Microbiology, vol. 64, No. 3, pp. 1079-1085 (1998).
U.S. Office Action, U.S. Appl. No. 13/255,239 dated Dec. 5, 2012, 12 pages.
Vazquez, et al., "Silica-supported Heteropolyacids as Catalysts in Alcohol Dehydration Reactions", Journal of Molecular Catalysis A: Chemical 161 (2000) pp. 223-232, 10 pages.

* cited by examiner

*Primary Examiner* — In Suk Bullock
*Assistant Examiner* — Sharon Pregler
(74) *Attorney, Agent, or Firm* — Rankin, Hill & Clark LLP

(57) ABSTRACT

A novel olefin production process of the invention can be established as an industrial and practical process of producing an olefin with high selectivity by directly reacting a ketone and hydrogen in a single reaction step. In particular, a novel olefin production process is provided in which propylene is obtained with high selectivity by directly reacting acetone and hydrogen. An olefin production process of the invention includes reacting a ketone and hydrogen at a reaction temperature in the range of 50 to 300° C. in the presence of a Cu-containing hydrogenation catalyst and a solid acid substance.

19 Claims, No Drawings

OLEFIN PRODUCTION PROCESS

FIELD OF THE INVENTION

The present invention relates to processes for producing an olefin by reacting a ketone and hydrogen. In more detail, the invention relates to processes for producing an olefin with high selectivity from a ketone and hydrogen as starting materials in a single reaction step by using a Cu-containing hydrogenation catalyst and a solid acid substance.

BACKGROUND OF THE INVENTION

A reaction between benzene and propylene gives cumene. Oxidation of cumene results in cumene hydroperoxide. The cumene hydroperoxide is acid decomposed into phenol and acetone. A combination of these known reactions is the cumene process and is currently a mainstream process for the production of phenol.

In the cumene process, acetone is byproduced. The cumene process is valuable when both phenol and acetone are required. However, if the acetone produced is in excess of demand, the economic efficiency is deteriorated due to the price difference between acetone and starting material propylene. Methods have been then proposed in which acetone byproduced is reused as a material in the cumene process through various reactions.

Acetone is readily hydrogenated to isopropyl alcohol, and the isopropyl alcohol is dehydrated to propylene. Patent Document 1 discloses a process in which acetone is reused as a material in the cumene process, in detail cumene is produced by reacting benzene and propylene obtained from acetone as described above.

In the reuse of acetone, an industrial and practical process should be established which is capable of producing propylene from acetone with high selectivity. Further, the establishment of industrial and practical processes capable of producing not only propylene but other olefins from general ketones with high selectivity is also valuable in various other processes.

Patent Document 2 discloses a process in which propylene is obtained through hydrogenation of acetone at 400° C. in the presence of a catalyst containing Cu (25%), zinc oxide (35%) and aluminum oxide (40%). However, this process involves high reaction temperature and is insufficient in heat efficiency.

Patent Document 1: JP-A-H02-174737
Patent Document 2: East German Patent DD84378

SUMMARY OF THE INVENTION

It is therefore an object of the present invention to provide a novel olefin production process that can be established as an industrial and practical process capable of producing an olefin with high selectivity by directly reacting a ketone and hydrogen in a single reaction step. In particular, an object of the invention is to provide a novel olefin production process in which propylene is obtained with high selectivity by directly reacting acetone and hydrogen.

The present inventors studied diligently to achieve the above objects. They have then found that an olefin are produced with high selectivity from a ketone and hydrogen as starting materials in a single reaction step by using a Cu-containing hydrogenation catalyst and a solid acid substance as catalysts.

The olefin production processes according to the invention are as described in (1) to (9) below.

(1) An olefin production process comprising reacting a ketone and hydrogen at a reaction temperature in the range of 50 to 300° C. in the presence of a Cu-containing hydrogenation catalyst and a solid acid substance.

(2) The olefin production process described in (1) above, wherein the Cu-containing hydrogenation catalyst further contains at least one element belonging to Group IIIA, Group IIB and Group VIB.

(3) The olefin production process described in (1) above, wherein the solid acid substance is a zeolite.

(4) The olefin production process described in (3) above, wherein the zeolite is a zeolite possessing a pore of ten to twelve-membered oxygen ring.

(5) The olefin production process described in (4) above, wherein the zeolite possessing a pore of ten to twelve-membered oxygen ring is a β-zeolite.

(6) The olefin production process described in (1) above, wherein the reaction is carried out in a fixed bed reactor, and the Cu-containing hydrogenation catalyst is packed in an inlet side of the reactor and the solid acid substance is packed in an outlet side of the reactor.

(7) The olefin production process described in (1) above, wherein the ketone is acetone and the olefin is propylene.

(8) An olefin production process comprising supplying a ketone, hydrogen and water to a reactor packed with a Cu-containing hydrogenation catalyst and a solid acid substance and reacting the ketone with hydrogen at a reaction temperature in the range of 50 to 300° C., the molar ratio of water to the ketone supplied (water/ketone) being in the range of 0.01 to 1.0.

(9) The olefin production process described in (1) above, wherein the ketone is an acetone obtained with an isopropyl alcohol-producing bacterium that produces isopropyl alcohol and acetone from a plant-derived material, and the olefin is propylene.

ADVANTAGEOUS EFFECTS OF THE INVENTION

The novel olefin production processes of the invention can be established as industrial and practical processes of producing an olefin with high selectivity by directly reacting a ketone and hydrogen in a single reaction step. In particular, propylene is obtained with high selectivity by directly reacting acetone and hydrogen according to the novel process of the invention.

PREFERRED EMBODIMENTS FOR CARRYING OUT THE INVENTION

In the olefin production processes of the invention, a ketone and hydrogen are reacted at a reaction temperature in the range of 50 to 300° C. in the presence of a Cu-containing hydrogenation catalyst and a solid acid substance.

In a preferred embodiment of the olefin production process, a ketone, hydrogen and water are supplied to a reactor packed with a Cu-containing hydrogenation catalyst and a solid acid substance and the ketone is reacted with hydrogen at a reaction temperature in the range of 50 to 300° C., and the molar ratio of water to the ketone supplied (water/ketone) is in the range of 0.01 to 1.0.

In the specification, the Cu-containing hydrogenation catalyst may be simply referred to as the hydrogenation catalyst.

The two catalysts, namely, the hydrogenation catalyst and the solid acid substance, may be used in any manner without limitation. For example, the solid acid substance that is an acid catalyst component and the hydrogenation catalyst may be physically mixed on a catalyst particle level with a centimeter size. Alternatively, the catalysts may be finely pulverized and mixed together, and the mixture may be formed into catalyst particles with a centimeter size. Still alternatively, the hydrogenation catalyst may be supported on the solid acid substance as a carrier, or the solid acid substance may be supported on the hydrogenation catalyst as a carrier.

In the olefin production processes of the invention, it is assumed that a ketone is hydrogenated into an alcohol under the catalysis of the Cu-containing hydrogenation catalyst, and the alcohol is then dehydrated by the action of the solid acid substance to produce an olefin. When the olefin is propylene for example, reactions are considered to take place such that acetone is hydrogenated into isopropyl alcohol under the catalysis of the hydrogenation catalyst and the isopropyl alcohol is dehydrated by the solid acid substance to produce propylene and water.

That is, it is considered that the hydrogenation reaction and the dehydration reaction take place stepwise in the olefin production processes of the invention. Accordingly, the catalysts may form distinct catalyst layers in the appropriate order of reactions, or the hydrogenation catalyst and the solid acid substance may be mixed in a graded mixing ratio.

Water lowers the activity of the solid acid substances such as zeolites in working as acid catalysts. Therefore, in the conventional reactions involving the solid acid substances, water have been avoided or removed in the reaction system in order to maintain the activity of the acid catalysts.

However, according to the finding by the present inventors, a specific amount of water added to a reactor increases the olefin selectivity while the acid catalysts maintain their activity in contrast to the traditional belief that water decreases the activity of the acid catalysts.

The ketones used in the invention may be selected appropriately depending on the target olefins. For example, acetone is used to produce propylene, and methyl ethyl ketone is used to obtain 1-butene.

The olefin production processes of the invention are suited for the production of propylene from acetone.

The ketones may be obtained by any methods without limitation. For example, acetone that is byproduced in the production of phenol, and methyl ethyl ketone from dehydrogenation of 2-butanol may be used. When the ketone is acetone, an acetone may be used which is obtained with an isopropyl alcohol-producing bacterium that produces isopropyl alcohol and acetone from a plant-derived material.

The plant-derived materials are not particularly limited as long as they are carbon sources obtained from plants and are metabolized to isopropyl alcohol by bacteria. The plant-derived materials include organs such as roots, stems, trunks, branches, leaves, flowers and seeds, plants or plant organs having these organs, or degradation products of thereof. Further, the term plant-derived materials in the invention includes carbon sources obtained from plants, plant organs or degradation products thereof that can be used as carbon sources by bacteria in culture. Examples of the carbon sources as the plant-derived materials include sugars such as starch, glucose, fructose, sucrose, xylose and arabinose, or plant degradation products and cellulose hydrolysates containing large amounts of the above sugars. Further, the carbon sources in the invention include plant oil-derived glycerols and fatty acids. Preferred plant-derived materials include agricultural crops such as grain, and corn, rice, wheat, bean, sugarcane, beet and cotton. These materials may be used in any form without limitation, and for example may be used in the form of unprocessed product, squeezed juice or milled product. In an embodiment, the carbon sources as described above may be used directly.

The isopropyl alcohol-producing bacteria are not limited as long as they can produce isopropyl alcohol and acetone from the plant-derived materials. For example, bacteria that are cultured on the plant-derived materials and secrete isopropyl alcohol and acetone in the culture medium after a given time may be used. Such isopropyl alcohol-producing bacteria are described in literature such as WO 2009/008377, Chinese Patent Application No. CN1043956A, JP-A-S61-67493, and Applied and Environmental Microbiology, Vol. 64, No. 3, pp. 1079-1085 (1998). In particular, isopropyl alcohol-producing bacteria described in WO 2009/008377 are preferred.

The isopropyl alcohol-producing bacteria described in WO 2009/008377 are given acetoacetic acid decarboxylase activity, isopropyl alcohol dehydrogenase activity, CoA transferase activity and thiolase activity.

The words the bacteria are "given" the activities mean that an enzyme-encoding gene is introduced into the host bacteria from outside the bacteria, and that an enzyme gene possessed by the host bacteria on the genome is strongly expressed by enhancing the promoter activity or replacing the promoter with another promoter.

In a preferred embodiment, the acetoacetic acid decarboxylase activity, the isopropyl alcohol dehydrogenase activity, the CoA transferase activity and the thiolase activity are obtained by the introduction of a gene that encodes an enzyme derived from at least one selected from the group consisting of *Clostridium* bacteria, *Bacillus* bacteria and *Escherichia* bacteria.

In a more preferred embodiment, the acetoacetic acid decarboxylase activity and the isopropyl alcohol dehydrogenase activity are obtained by the introduction of a gene that encodes an enzyme derived from *Clostridium* bacteria, and the CoA transferase activity and the thiolase activity are obtained by the introduction of a gene that encodes an enzyme derived from *Escherichia* bacteria.

In a particularly preferred embodiment, the acetoacetic acid decarboxylase activity is obtained by the introduction of a gene that encodes an enzyme derived from *Clostridium acetobutylicum*, the isopropyl alcohol dehydrogenase activity is obtained by the introduction of a gene that encodes an enzyme derived from *Clostridium beijerinckii*, and the CoA transferase activity and the thiolase activity are obtained by the introduction of a gene that encodes an enzyme derived from *Escherichia coli*.

In another preferred embodiment, the acetoacetic acid decarboxylase activity, the isopropyl alcohol dehydrogenase activity, the CoA transferase activity and the thiolase activity are each obtained by the introduction of a gene that encodes an enzyme derived from *Clostridium* bacteria.

The isopropyl alcohol-producing bacteria are preferably *Escherichia coli*.

The production of isopropyl alcohol and acetone from the plant-derived materials by the isopropyl alcohol-producing bacteria usually gives byproducts such as water and carboxylic acids. When an acetone obtained from the plant-derived material with the isopropyl alcohol-producing bacteria is used as the ketone in the invention, the acetone may be purified to high purity by removing the isopropyl alcohol, water and other byproducts from the product.

Alternatively, the isopropyl alcohol and acetone in the product may be concentrated to a high concentration while the byproducts are removed. In this case, the acetone is supplied to a reactor together with the isopropyl alcohol and water. The isopropyl alcohol is dehydrated by the solid acid substance, producing propylene and water.

The hydrogen used in the invention may be a molecular hydrogen gas or a hydrocarbon such as cyclohexane that generates hydrogen when subjected to reaction conditions.

Theoretically, the hydrogen may be used at least in an equimolar amount relative to the ketone. From the viewpoint of separation and recovery, the hydrogen may be preferably used in an equimolar to ten-fold molar amount, and more preferably in an equimolar to 5-fold molar amount relative to the ketone. For example, the hydrogen supply amount per unit time may be controlled in this range relative to the ketone supply amount per unit time. When the ketone conversion is desired to be 100% or less, the hydrogen amount may be controlled less than the equimolar amount relative to the ketone. In the invention, the hydrogen reacts with the oxygen atom in the ketone to form water, and the water produced may be recovered from a reactor outlet. An excess of hydrogen over the ketone is not substantially consumed as long as undesirable side reactions take place.

The hydrogen gas is generally supplied to a reactor continuously, but the supply methods are not particularly limited thereto. In an embodiment, the hydrogen gas may be supplied intermittently such that the hydrogen is supplied at the initiation of the reaction and the supply is suspended during the reaction and restarted after a prescribed time. In the case of a liquid-phase reaction, the hydrogen gas may be supplied while being dissolved in a solvent. In a recycle process, hydrogen gas recovered from the column top together with low-boiling fractions may be isolated and resupplied. The pressure of the hydrogen supplied is generally equal to the pressure in the reactor, but may be appropriately adjusted depending on the hydrogen supply methods.

When water is used in the olefin production processes of the invention, the ketone and water are supplied to a reactor packed with the hydrogenation catalyst and the solid acid substance such that the water/ketone molar ratio is in the range of 0.01 to 1.0, preferably 0.02 to 0.9, and more preferably 0.05 to 0.8. For example, water may be supplied in this molar ratio per unit time relative to the ketone supply amount per unit time. This molar ratio ensures that the olefin selectivity is improved by the water without lowering the activity of the acid catalyst.

In an embodiment for carrying out the invention, the reaction may be carried out in a diluted reaction system by supplying a solvent or a gas that is inert to the catalysts and the starting materials (ketone and hydrogen, or ketone, hydrogen and water).

In the olefin production processes of the invention, the reaction may be carried out by any methods under any conditions without limitation. Exemplary conditions and methods are described below.

The contact between the starting materials, i.e., ketone and hydrogen, and the supply of water may take place in a gas-liquid countercurrent flow or a gas-liquid co-current flow. The liquid and gas directions are not limited. These directions may be descending liquid/ascending gas, ascending liquid/descending gas, ascending gas/ascending liquid, or descending gas/descending liquid.

The reaction temperature is in the range of 50 to 300° C., preferably 150 to 250° C., and more preferably 150 to 200° C. The reaction pressure is preferably in the range of 0.1 to 500 atm, and more preferably 0.5 to 100 atm.

<Solid Acid Substances>

Examples of the solid acid substances include usual solid acids such as metal oxides including zeolite, silica, alumina, silica alumina, γ-alumina, titanium oxide, zinc oxide and zirconium oxide. Of these, zeolite is preferable.

An appropriate zeolite may be selected depending on the molecular diameter of an alcohol expected as an intermediate in the reaction and the target olefin.

In particular, zeolite possessing a pore of ten to twelve-membered oxygen ring is preferred. Examples of the zeolites possessing a pore of ten to twelve-membered oxygen ring include ferrierite, heulandites, ZSM-5, ZSM-11, ZSM-12, NU-87, theta-1, weinbergerite, X-type zeolite, Y-type zeolite, USY-type zeolite, mordenite, dealuminated mordenite, β-zeolite, MCM-22, MCM-36 and MCM-56. Of these, β-zeolite is preferable.

In the zeolite, the composition ratio between silicon and aluminum (silicon/aluminum) is preferably in the range of 2/1 to 200/1, and in view of activity and heat stability, particularly preferably in the range of 5/1 to 100/1. Further, isomorphously substituted zeolites in which aluminum in the zeolite skeleton is substituted with other metal such as Ga, Ti, Fe, Mn or B may be used. Furthermore, metal ion-modified zeolites may be used.

The shape of the solid acid substances is not particularly limited, and the solid acid substances may be in the form of sphere, cylindrical column, extrudate or crushed particles. The size of the particles of the solid acid substances is not particularly limited. Generally, the particle diameter may range from 0.01 to 100 mm depending on the size of a reactor.

The solid acid substances may be used singly, or two or more kinds may be used in combination.

<Cu-Containing Hydrogenation Catalysts>

The Cu-containing hydrogenation catalyst may contain Cu as the metal element or as a metal compound. Examples of the metal compounds include metal oxides such as CuO and $Cu_2O$; and metal chlorides such as $CuCl_2$. The catalysts may be supported on carriers.

Preferably, the Cu-containing hydrogenation catalysts further contain at least one element belonging to Group IIIA, Group IIB and Group VIE. Preferred Group IIIA elements include Al and In; preferred Group IIB elements include Zn; and preferred Group VIB elements include Cr and Mo. Examples of such hydrogenation catalysts include copper-containing catalysts such as copper chromium catalysts, Raney copper catalysts and copper zinc catalysts.

Higher activity and olefin selectivity tend to be obtained by using Cu-containing hydrogenation catalysts that contain metal salts such as $PbSO_4$, $FeCl_2$ and $SnCl_2$; alkali metals such as K and Na, and alkali metal salts; and $BaSO_4$.

Commercially available Cu-containing hydrogenation catalysts include $CuO$—$ZnO$—$Al_2O_3$ and $CuO$—$Cr_2O_3$—$BaO$.

The shape of the hydrogenation catalysts is not particularly limited, and the hydrogenation catalysts may be in the form of sphere, cylindrical column, extrudate or crushed particles. The size of the particles of the hydrogenation catalysts is not particularly limited. Generally, the particle diameter may range from 0.01 to 100 mm depending on the size of a reactor.

<Usage of Hydrogenation Catalysts and Solid Acid Substances>

In the olefin production processes of the invention, the ketone, hydrogen and optionally water are supplied to a reactor packed with the hydrogenation catalyst and the solid acid substance and the ketone is reacted with hydrogen. The total amount of the hydrogenation catalyst and the solid acid substance in the reactor (hereinafter, also the catalyst amount) is not particularly limited. In an embodiment in which the reaction is performed in a fixed bed flow apparatus equipped with a fixed bed reactor, the catalyst amount may be such that the supply amount (weight) of the starting material ketone per hour divided by the catalyst amount (weight), namely, the weight hourly space velocity (WHSV) is preferably in the range of 0.1 to 200/h, and more preferably 0.2 to 100/h.

The weight ratio of the solid acid substance and the hydrogenation catalyst is not particularly limited, but the solid acid substance:hydrogenation catalyst weight ratio is usually in the range of 1:0.01 to 1:100, and preferably 1:0.05 to 1:50. An excessively small amount of the solid acid substance results in insufficient dehydration reaction and low olefin yield, causing economic disadvantages. An excessively large amount of the solid acid substance is also uneconomical because the ketone conversion is lowered.

When water is used in the processes of the invention, the hydrogenation catalyst and the solid acid substance are preferably dehydrated by known methods in order to control strictly the water content in the reactor. In the case of a fixed bed reactor, the hydrogenation catalyst and the solid acid substance packed therein may be dehydrated by keeping the temperature at 300° C. or above for at least 10 minutes while passing an inert gas (for example nitrogen or helium) through the reactor. To develop the activity of the hydrogenation catalyst, the dehydration treatment may be followed by a treatment under a stream of hydrogen.

In the event that the catalyst activity is lowered after a time of reaction, the hydrogenation catalyst and the solid acid substance may be regenerated by known methods to recover the activity.

In the invention, the hydrogenation catalyst and the solid acid substance may be used in any manner without limitation. The hydrogenation catalyst and the solid acid substance may be physically mixed on a catalyst particle level with a centimeter size. Alternatively, the catalysts may be finely pulverized and mixed together, and the mixture may be formed into catalyst particles with a centimeter size. Still alternatively, the hydrogenation catalyst may be supported on the solid acid substance as a carrier, or the solid acid substance may be supported on the hydrogenation catalyst as a carrier.

In a particularly preferred embodiment, the Cu-containing hydrogenation catalyst and zeolite as the solid acid substance are used. The Cu-containing hydrogenation catalyst may be supported on the zeolite. Such supported catalysts may be prepared by soaking zeolite in an aqueous solution of a copper salt such as copper nitrate and calcining the zeolite. Alternatively, copper may be bonded with an organic molecule ligand to become soluble inorganic solvents, and zeolite may be soaked in a solution of the copper-ligand complex in an organic solvent and thereafter calcined. Taking advantage of the characteristic that some of the complexes are vaporized under vacuum, such complexes may be supported on zeolite by deposition or the like. Further, a coprecipitation method may be adopted in which zeolite is obtained from a corresponding metal salt in the presence of a copper salt as the hydrogenation catalyst and thereby the carrier synthesis and the supporting of the hydrogenation catalyst are carried out simultaneously.

Other carriers for the hydrogenation catalysts include silica, alumina, silica alumina, titania, magnesia, silica magnesia, zirconia, zinc oxide, carbon (activated carbon), acid clay and diatomaceous earth. In a preferred embodiment, at least one is selected from silica, alumina, silica alumina, titania, magnesia, silica magnesia, zirconia, zinc oxide and carbon (activated carbon). Some of these carriers function as solid acid substances. When such carriers are used, the hydrogenation catalysts are supported on the solid acid substances as carriers.

Examples of the reactors used in the invention include fixed bed reactors and fluidized bed reactors. Fixed bed reactors are preferable from the viewpoint of the prevention of catalyst abrasion or particle size reduction.

In the invention, the hydrogenation catalysts and the solid acid substances may be packed in the reactor by any methods without limitation. In the case of fixed bed reactors, however, the packing mode of the hydrogenation catalyst and the solid acid substance may greatly affect the reaction results. As described hereinabove, the hydrogenation reaction and the dehydration reaction probably take place stepwise in the invention. Accordingly, the catalysts are preferably packed in the appropriate order of reactions in order to catalyze the reactions effectively and prevent undesired side-reactions.

In particular, increasing the hydrogen pressure or the reaction temperature to accelerate the reaction rate usually involves undesired side-reactions that are not observed at low hydrogen pressure or low reaction temperature. In such cases, the reaction results can be greatly influenced by the catalyst packing manner.

Accordingly, the catalysts may be packed in the appropriate order of reactions, or the hydrogenation catalyst and the solid acid substance may be mixed in a graded mixing ratio. For example, the hydrogenation catalyst and the solid acid substance may be packed in the reactor in a manner such that: (1) the hydrogenation catalyst and the solid acid substance are mixed together and packed in the reactor; (2) the hydrogenation catalyst forms a layer on an upstream side (an inlet side) of the reactor and the solid acid substance forms a layer on a downstream side (an outlet side) of the reactor; (3) the solid acid substance supporting the hydrogenation catalyst is packed; (4) the hydrogenation catalyst forms a layer on an upstream side (an inlet side), and the solid acid substance and the hydrogenation catalyst form a layer on a downstream side (an outlet side); (5) the hydrogenation catalyst forms a layer on an upstream side (an inlet side) and the solid acid substance supporting the hydrogenation catalyst forms a layer on a downstream side (an outlet side); (6) the hydrogenation catalyst and the solid acid substance form a layer on an upstream side (an inlet side) and the solid acid substance forms a layer on a downstream side (an outlet side); or (7) the solid acid substance supporting the hydrogenation catalyst forms a layer on an upstream side (an inlet side) and the solid acid substance forms a layer on a downstream side (an outlet side). Here, the term upstream side means an inlet side of the reactor, in other words, this term indicates that the starting materials are passed through the layer in the first half of the reaction. The term downstream side means an outlet side of the reactor, in other words, this term indicates that the starting materials, intermediates and reaction products are passed through the layer in the last half of the reaction.

To maintain the olefin production output, two or three reactors may be arranged in parallel to adopt a merry-go-round system in which the catalyst in one reactor is regenerated while the reaction is continuously carried out in the remaining one or two reactors. When the process involves three reactors, two of these reactors may be connected in series to stabilize the production output. When the reaction is carried out in a fluidized bed flow reaction system or in a moving bed reaction system, part or the whole of the catalysts may be withdrawn from the reactor continuously or intermittently while a corresponding amount of the catalysts are newly added to maintain the activity at a constant level.

EXAMPLES

The present invention will be described in greater detail by examples hereinbelow without limiting the scope of the invention.

Example 1

A fixed bed reaction apparatus was used which was equipped with a high-pressure feed pump, a high-pressure hydrogen mass flow controller, a high-pressure nitrogen mass flow controller, an electric furnace, a reactor having a catalyst-packing part, and a back pressure valve. A pressurized liquid-phase downflow reaction was carried out in the reaction apparatus.

The reactor was a SUS 316 reactor having an inner diameter of 1 cm. From the outlet of the reactor, 1.0 g of a copper/zinc catalyst powder (Shift Max 210 manufactured by Sud-Chemie AG, containing 32-35% by mass of copper, 35-40% by mass of zinc and 6-7% by mass of aluminum, classified to 250-500 µm) was packed to form a catalyst layer on an upstream side. Quartz wool as a separator between the catalyst layers was packed. Thereafter, 1.0 g of β-zeolite (manufactured by JGC Catalysts and Chemicals Ltd., compacted at 20 MPa and classified to 250-500 µm) was packed to form a catalyst layer on a downstream side.

The pressure was increased to 2.5 MPa with hydrogen, and reduction treatment was carried out by feeding hydrogen at 20 ml/min from the reactor inlet at 200° C. for 3 hours. Under a stream of hydrogen at 20 ml/min, the temperature was then lowered to 175° C. and acetone was passed from the reactor inlet at 0.75 g/h.

Nitrogen was fed at 50 ml/min in between the reactor outlet and the back pressure valve by means of the high-pressure nitrogen mass flow controller. A gas chromatograph (GC) was provided at a downstream from the back pressure valve, and the products were quantitatively determined on line.

The reaction results are set forth in Table 1.

TABLE 1

| Reaction temperature | Acetone conversion (%) | Selectivity (%)/based on acetone | | | | |
|---|---|---|---|---|---|---|
| | | Propylene | Isopropanol | Diisopropanol | Propane | Others |
| Ex. 1 175° C. | 97.1 | 91.8 | 3.0 | 2.6 | 1.5 | 1.1 |

Example 2

A fixed bed reaction apparatus was used which was equipped with a high-pressure feed pump, a high-pressure hydrogen mass flow controller, a high-pressure nitrogen mass flow controller, an electric furnace, a reactor having a catalyst-packing part, and a back pressure valve. A pressurized liquid-phase downflow reaction was carried out in the reaction apparatus.

The reactor was a SUS 316 reactor having an inner diameter of 1 cm. From the outlet of the reactor, a catalyst mixture was packed to form a catalyst layer wherein the catalyst mixture had been prepared by sufficiently mixing 0.3 g of a copper/zinc catalyst powder (Shift Max 210 manufactured by Sud-Chemie AG, containing 32-35% by mass of copper, 35-40% by mass of zinc and 6-7% by mass of aluminum, classified to 250-500 µm) and 0.6 g of β-zeolite (manufactured by JGC Catalysts and Chemicals Ltd., compacted at 20 MPa and classified to 250-500 µm).

The pressure was increased to 3.0 MPa with hydrogen, and acetone was passed at 0.30 g/h from the reactor inlet at 180° C. under a stream of hydrogen at 12 ml/min.

Nitrogen was fed at 50 ml/min in between the reactor outlet and the back pressure valve by means of the high-pressure nitrogen mass flow controller. A gas chromatograph was provided at a downstream from the back pressure valve, and the products were quantitatively determined on line.

The reaction results are set forth in Table 2.

TABLE 2

| | Reaction temperature | Hydrogen/acetone molar ratio | Acetone conversion (%) | Selectivity (%)/acetone | | Selectivity (%)/(acetone-IPA-DIPE) | | | |
|---|---|---|---|---|---|---|---|---|---|
| | | | | IPA | DIPS | Propylene | Propane | Propylene dimer | Others |
| Ex. 2 | 180° C. | 6 | 90.1 | 1.6 | 0.0 | 67.7 | 29.4 | 2.9 | 0.0 |

IPA = isopropyl alcohol
DIPE = diisopropyl ether

Example 3

A fixed bed reaction apparatus was used which was equipped with a high-pressure feed pump, a high-pressure hydrogen mass flow controller, a high-pressure nitrogen mass flow controller, an electric furnace, a reactor having a catalyst-packing part, and a back pressure valve. A pressurized liquid-phase downflow reaction was carried out in the reaction apparatus.

The reactor was a SUS 316 reactor having an inner diameter of 1 cm. From the outlet of the reactor, 1.0 g of a copper/zinc catalyst powder (Shift Max 210 manufactured by Sud-Chemie AG, containing 32-35% by mass of copper, 35-40% by mass of zinc and 6-7% by mass of aluminum, classified to 250-500 µm) as a hydrogenation catalyst was packed to form a catalyst layer on an upstream side. Quartz wool as a separator between the catalyst layers was packed. Thereafter, 1.0 g of β-zeolite (manufactured by JGC Catalysts and Chemicals Ltd., compacted at 20 MPa and classified to 250-500 µm) as a solid acid substance was packed to form a catalyst layer on a downstream side.

The pressure was increased to 2.5 MPa with hydrogen, and reduction treatment was carried out by feeding hydrogen at 20 ml/min from the reactor inlet at 200° C. for 3 hours. Under a stream of hydrogen at 20 ml/min, the temperature was then lowered to 180° C. From the reactor inlet, acetone was passed at 0.60 g/h and water at 0.019 g/h, whereby the water/acetone molar ratio was 0.1.

Nitrogen was fed at 50 ml/min in between the reactor outlet and the back pressure valve by means of the high-pressure nitrogen mass flow controller. A gas chromatograph was provided at a downstream from the back pressure valve, and the products were quantitatively determined on line. The reaction results are set forth in Table 3.

Example 4

The procedures in Example 3 were repeated, except that water was passed at 0.056 g/h, whereby the water/acetone molar ratio was 0.3. The reaction results are set forth in Table 3.

Example 5

The procedures in Example 3 were repeated, except that water was passed at 0.074 g/h, whereby the water/acetone molar ratio was 0.4. The reaction results are set forth in Table 3.

Example 6

The procedures in Example 3 were repeated, except that water was passed at 0.186 g/h, whereby the water/acetone molar ratio was 1.0. The reaction results are set forth in Table 3.

Example 7

The procedures in Example 3 were repeated, except that acetone was passed at 0.60 g/h from the reactor inlet and water was not passed. The reaction results are set forth in Table 3.

Here, a production apparatus 10 as illustrated in FIG. 1 of WO 2009/008377 was used. A culture tank, a trap tank, an injection tube, a connection tube and a discharge tube were all made of glass. The culture tank and the trap tank each had a capacity of 3 L. The trap tank contained 1.8 L of water as trap liquid (trap water). The trap water had been cooled to 10° C.

A waste tube was attached to the culture tank, and the increase of the culture liquid by the feed of sugars or neutralizers was controlled by appropriately discharging the culture liquid from the culture tank.

The pGAP-Iaaa/B strain was inoculated in a 100 mL conical flask that contained 25 mL of LB Broth, Miller culture liquid (Difco 244620) containing 50 μg/mL of ampicillin, and was pre-cultured overnight with stirring at 120 rpm and a culture temperature of 35° C. The whole amount of the culture liquid was transferred to the 3 L culture tank (fermentor BMS-PI manufactured by ABLE & Biott Co., Ltd.) that contained 1475 g of a culture medium having the composition below. The culture liquid was cultured with aeration at 1.5 L/min at atmospheric pressure, a stirring speed of 5.50 rpm, a culture temperature of 35° C. and pH of 7.0 (adjusted with an aqueous $NH_3$ solution). A 45 wt/wt % aqueous glucose solution was added at 7.5 g/L/h for 8 hours from the initiation of the culture. Afterward, the 45 wt/wt % aqueous glucose solution was added at 15 g/L/h. The trap water after 130 hours after the culture initiation was analyzed by GC and was found to contain 1.6 wt % of acetone and 5.6 wt % of isopropyl alcohol.

<Culture Medium Composition>

Corn steep liquor (NIHON SHOKUHIN KAKO CO., LTD.): 20 g/L

TABLE 3

| | Water/acetone molar ratio | Acetone conversion (%) | Selectivity (%)/acetone | | Selectivity (%)/(acetone-IPA-DIPE) | | | |
|---|---|---|---|---|---|---|---|---|
| | | | IPA | DIPE | Propylene | Propane | Propylene dimer | Others |
| Ex. 3 | 0.1 | 98.6 | 6.2 | 1.0 | 98.0 | 0.8 | 0.7 | 0.5 |
| Ex. 4 | 0.3 | 98.5 | 6.6 | 1.2 | 98.6 | 0.6 | 0.6 | 0.2 |
| Ex. 5 | 0.4 | 98.4 | 8.9 | 1.1 | 98.7 | 0.6 | 0.6 | 0.1 |
| Ex. 6 | 1.0 | 98.4 | 24.0 | 3.0 | 99.0 | 0.5 | 0.4 | 0.1 |
| Ex. 7 | 0.0 | 98.0 | 4.4 | 1.0 | 97.0 | 0.8 | 1.2 | 1.0 |

IPA = isopropyl alcohol
DIPE = diisopropyl ether

In the tables above, the "selectivity (%)/acetone" indicates acetone conversions (molar percentages) to the products relative to the amount of raw material acetone, and the "selectivity (%)/(acetone-IPA-DIPE)" indicates acetone conversions (molar percentages) to the products relative to the amount of raw material acetone after deduction of the acetone conversions to IPA and DIPS produced. Here, IPA and DIPS are intermediates in the series of hydrogenation and dehydration reactions.

The results in Table 3 show that water prevents the formation of undesired byproducts such as propylene dimers, and propylene can be produced with high selectivity by supplying water.

Example 8

(Production of Isopropyl Alcohol and Acetone)

Isopropyl alcohol was produced using isopropyl alcohol-producing *Escherichia coli* bacteria (*Escherichia coli* pGAP-Iaaa/B strain) described in Example 4 of WO 2009/008377.

$Fe_2SO_4.7H_2O$: 0.09 g/L
$K_2HPO_4$: 2 g/L
$KH_2PO_4$: 2 g/L
$MgSO_4.7H_2O$: 2 g/L
$(NH_4)_2SO_4$: 2 g/L
ADEKA NOL LG126 (ADEKA CORPORATION): 0.6 g/L
Water: balance (Production of Propylene)

The aqueous solution containing isopropyl alcohol and acetone (the trap water after 130 hours from the culture initiation) was distilled to concentrate isopropyl alcohol and acetone.

In detail, 1947.0 g of the aqueous solution was passed at 500 ml/h through a column packed with 240 mL of a cation exchange resin (AMBERLYST 31WET manufactured by ORGANO CORPORATION), thereby removing residual ammonia. The treated liquid was distilled at normal pressure to separate fractions having a boiling point of 53 to 81.6° C.

Gas chromatography showed that the fractions contained 22.6 wt % of acetone, 58.7 wt % of isopropyl alcohol and a balance of water.

The fractions were subjected to a pressurized liquid-phase downflow reaction using a fixed bed reaction apparatus which was equipped with a high-pressure feed pump, a high-pressure hydrogen mass flow controller, a high-pressure nitrogen mass flow controller, an electric furnace, a reactor having a catalyst-packing part, and a back pressure valve.

The reactor was a SUS 316 reactor having an inner diameter of 1 cm. From the outlet of the reactor, 0.5 g of a copper/zinc catalyst powder (Shift Max 210 manufactured by Sud-Chemie AG, containing 32-35% by mass of copper, 35-40% by mass of zinc and 6-7% by mass of aluminum, classified to 250-500 μm) was packed to form a catalyst layer on an upstream side. Quartz wool as a separator between the catalyst layers was packed. Thereafter, 1.5 g of β-zeolite (manufactured by JGC Catalysts and Chemicals Ltd., compacted at 20 MPa and classified to 250-500 μm) was packed to form a catalyst layer on a downstream side.

The pressure was increased to 2.5 MPa with hydrogen, and reduction treatment was carried out by feeding hydrogen at 20 ml/min from the reactor inlet at 200° C. for 3 hours. Under a stream of hydrogen at 20 ml/min, the temperature was then lowered to 180° C. and the fractions were passed from the reactor inlet at 0.60 g/h.

Nitrogen was fed at 200 ml/min in between the reactor outlet and the back pressure valve by means of the high-pressure nitrogen mass flow controller. A gas-liquid separation tube was provided immediately downstream the back pressure valve. The gas component and the liquid component were analyzed by gas chromatography to quantitatively determine the products. The reaction results are set forth in Table 4.

TABLE 4

| | Residual ratio/(acetone + IPA) | | | Selectivity of products (%)/(acetone-IPA-DIPE) | | | |
|---|---|---|---|---|---|---|---|
| Reaction time (h) | Acetone (%) | IPA (%) | DIPE (%) | Propylene | Propane | Propylene dimer | Others |
| 235 | 0.6 | 1.5 | 0.2 | 99.0 | 0.4 | 0.5 | 0.1 |

IPA = isopropyl alcohol
DIPE = diisopropyl ether

INDUSTRIAL APPLICABILITY

In the industrial and practical processes of the invention, ketone and hydrogen are reacted directly in a single reaction step to produce an olefin with high selectivity. By the process, propylene can be obtained directly from acetone occurring in the phenol production by the cumene process.

The invention claimed is:

1. An olefin production process comprising reacting an acetone and hydrogen at a reaction temperature in the range of 50 to 300° C. in the presence of a Cu-containing hydrogenation catalyst and a solid acid substance, wherein the solid acid substance is a β-zeolite.

2. The olefin production process according to claim 1, wherein the Cu-containing hydrogenation catalyst further contains at least one element belonging to Group IIIA, Group IIB and Group VIB.

3. The olefin production process according to claim 1, wherein the reaction is carried out in a single reactor, and the Cu-containing hydrogenation catalyst and the solid acid substance are separately packed in the single reactor.

4. The olefin production process according to claim 1, wherein the reaction is carried out in a single reactor, and the β-zeolite is supported on the Cu-containing hydrogenation catalyst in the single reactor.

5. The olefin production process according to claim 1, wherein the reaction is carried out in a single reactor, and the Cu-containing hydrogenation catalyst is supported on the β-zeolite in the single reactor.

6. The olefin production process according to claim 3, wherein the Cu-containing hydrogenation catalyst is packed in an inlet side of the reactor and the solid acid substance is packed in an outlet side of the reactor.

7. The olefin production process according to claim 1, wherein the olefin is propylene.

8. An olefin production process comprising supplying an acetone, hydrogen and water to a reactor packed with a Cu-containing hydrogenation catalyst and a solid acid substance and reacting the acetone with hydrogen at a reaction temperature in the range of 50 to 300° C., the molar ratio of water to the acetone supplied (water/acetone) being in the range of 0.01 to 1.0, wherein the solid acid substance is a β-zeolite.

9. The olefin production process according to claim 1, wherein the acetone is an acetone obtained with an isopropyl alcohol-producing bacterium that produces isopropyl alcohol and acetone from a plant-derived material, and the olefin is propylene.

10. The olefin production process according to claim 8, wherein the water in a liquid state is supplied to the reactor.

11. An olefin production process comprising:
supplying a mixture to a single reactor comprising a Cu-containing hydrogenation catalyst and β-zeolite, the mixture consisting of hydrogen in a gas state, acetone in a liquid state, water in a liquid state, optionally alcohol, and optionally an inert solvent, an inert gas, or combinations thereof, the molar ratio of water to the acetone (water/acetone) in the mixture being in the range of 0.01 to 1.0; and
reacting the acetone with the hydrogen in the single reactor at a reaction temperature in the range of 50 to 300° C.

12. The olefin production process according to claim 11, wherein the Cu-containing hydrogenation catalyst further contains at least one element belonging to Group IIIA, Group IIB and Group VIB.

13. The olefin production process according to claim 11, wherein the Cu-containing hydrogenation catalyst and the β-zeolite are separately packed in the single reactor.

14. The olefin production process according to claim 11, wherein the β-zeolite is supported on the Cu-containing hydrogenation catalyst in the single reactor.

15. The olefin production process according to claim 11, wherein the Cu-containing hydrogenation catalyst is supported on the β-zeolite in the single reactor.

16. The olefin production process according to claim 11, wherein the Cu-containing hydrogenation catalyst is packed in an inlet side of the reactor and the β-zeolite is packed in an outlet side of the reactor.

17. The olefin production process according to claim 11, wherein the single reactor comprises catalysts consisting of the Cu-containing hydrogenation catalyst and the β-zeolite.

18. The olefin production process according to claim 11, wherein the mixture consists of hydrogen in a gas state, acetone in a liquid state, water in a liquid state, and optionally an inert solvent, an inert gas, or combinations thereof.

19. The olefin production process according to claim 11, wherein the mixture consists of hydrogen in a gas state, acetone in a liquid state, and water in a liquid state.

* * * * *

UNITED STATES PATENT AND TRADEMARK OFFICE
CERTIFICATE OF CORRECTION

PATENT NO. : 8,680,355 B2
APPLICATION NO. : 13/131905
DATED : March 25, 2014
INVENTOR(S) : Ohkubo et al.

It is certified that error appears in the above-identified patent and that said Letters Patent is hereby corrected as shown below:

On the Title Page
Item [73] should read: Mitsui Chemicals, Inc., Tokyo (JP)

Signed and Sealed this
Twenty-fourth Day of June, 2014

Michelle K. Lee
*Deputy Director of the United States Patent and Trademark Office*